United States Patent [19]

McAleer et al.

[11] 4,301,250

[45] Nov. 17, 1981

[54] METHOD OF PRODUCING HEPATITIS B SURFACE ANTIGEN

[75] Inventors: William J. McAleer, Ambler; Henry Z. Markus, Wyncote, both of Pa.

[73] Assignee: Merck & Co., Inc., Rahway, N.J.

[21] Appl. No.: 90,169

[22] Filed: Nov. 2, 1979

[51] Int. Cl.³ .................... C12N 5/02; C12P 21/00; C12M 3/04

[52] U.S. Cl. .................................. 435/241; 435/68; 435/285

[58] Field of Search ............... 435/240, 241, 285, 68

[56] References Cited

U.S. PATENT DOCUMENTS 3,821,087  6/1974  Knazek et al. ..................... 435/285

OTHER PUBLICATIONS

Alexander, et. al., Studies on In Vitro Production of Hepatitis B Surface Antigen by a Human Hepatoma Cell Line, Perspectives in Virology, vol. 10, 1978, (pp. 103–120).

*Primary Examiner*—David M. Naff
*Attorney, Agent, or Firm*—Donald J. Perrella; Hesna J. Pfeiffer

[57] ABSTRACT

Hepatitis B surface antigen ($HB_sAg$) is produced in vitro in high titer and purity from tissue cultures of cells that shed $HB_sAg$ by growing the cells with a first incubation at elevated temperature followed by a second incubation at a lower elevated temperature.

9 Claims, No Drawings

METHOD OF PRODUCING HEPATITIS B SURFACE ANTIGEN

BACKGROUND OF THE INVENTION

Hepatitis B surface antigen (HB$_s$Ag) has been shown to be effective as a vaccine against hepatitis B disease. The usual source of this antigen is plasma obtained from donors, e.g., by phasmaphoresis. As a result the supply of plasma containing this antigen is uncertain and expensive as most plasma is free of HB$_s$Ag.

Attempts have been made heretofore to grow HB$_s$Ag in vitro. For example, it is known that in vitro tissue cultures of human hepatoma cells produce HB$_s$Ag in vitro although in only trace amounts and with no detectable complement fixation titer. Humans infected with hepatitis B disease, on the other hand, produce large amounts of HB$_s$Ag—about $10^{13}$ particles/ml with a complement fixation titer of about 256.

OBJECTS OF THE INVENTION

It is, accordingly, an object of the present invention to provide an in vitro tissue culture method for preparing HB$_s$Ag in high titer and purity. Another object is to provide an improved method for preparing HB$_s$Ag. A further object is to provide HB$_s$Ag free of Dane particles. These and other objects of the present invention will be apparent from the following description.

SUMMARY OF THE INVENTION

Hepatitis B surface antigen is produced in vitro in high titer and purity from tissue cultures of cells that shed HB$_s$Ag using a growth cycle having two different elevated temperature stages.

DETAILED DESCRIPTION

The present invention relates to a method of growing hepatitis B surface antigen (HB$_s$Ag) in vitro and, more particularly, to a method of growing HB$_s$Ag in vitro in high titer and purity using cells which shed HB$_s$Ag.

It has now been found that the yield of HB$_s$Ag from cells which shed HB$_s$Ag is increased markedly when the cells are grown in cell culture in vitro using a growth cycle having two different temperature ranges. Each temperature range is above room temperature and the first temperature range is higher than the second temperature range. The first temperature range is from 35° to about 38° C. while the second temperature range is from about 30° to 34° C. Preferably the first temperature is about 37° C. and the second temperature is about 32° C.

It has been found in addition that higher yields are obtained when caffeine is present in the in vitro cell culture nutrient medium in an amount effective to improve yield of HB$_s$Ag or when the in vitro cell culture is effected on a permeable membrane such as, for example, bundle of hollow fiber capillary units, or a dialysis membrane. The caffeine may be present in a level at which it exerts a dectable improvement in yield up to a level below which it exerts a toxic effect. Typically the caffeine is employed at from about 0.0001 M to about 0.007 M, preferably at from about 0.001 M to about 0.003 M.

Any cells which shed HB$_s$Ag may be used in the process of the present invention. Examples of such cells are some human hepatomas, high yielding clones from such human hepatomas, and liver cells from hepatitis B infected chimpanzees.

The human hepatoma tissue is grown in vitro in the presence of a nutrient medium. By a nutrient medium is meant one which permits growth of cells in vitro. Some specific nutrient media are, for example, Medium 199, Morgan et al., Proc. Soc. Exp. Biol. & Med.; 73:1-8, 1950; Basal Medium Eagle, Eagle Science, 122, 501-504, 1955; In Vitro, Vol. 6, No. 2, 1970; Dulbecco's Modified Eagle's Medium, Dulbecco et al., Virology, 8, 396, 1959; Smith et al., J. Virol. 12, 185-196, 1960; In Vitro, Vol. 6, No. 2, 1970; Minimum Essential Medium (Eagle), Science, 130, 432 (1959) and RPMI Media, Moore et al., 199, 519-524, 1967; In Vitro, Vol. 6, No. 2, 1970.

The cells which shed HB$_s$Ag may be grown in any suitable means known to the art such as, for example, tissue culture flasks, hollow fiber capillary units or dialysis membranes.

The hollow fiber capillary unit is formed of a plurality of anisotropic hollow fiber membranes which provide a matrix for the culture of cells and organ explants. A bundle of these capillaries forms a three dimensional vascular system which permits controlled perfusion of cell aggregates with nutrients, as well as exchange of excreted substances. The capillaries consist of a sponge-like body with a very thin (0.5-1 μm), smooth layer of extremely fine, controlled pore size (approximate range: 0.001-0.01 μm) of the lumen side. From that surface outward, the pores become increasingly larger 5-10 μm at the perimeter. This structure provides a unique combination of selectively and extremely high permeability to liquids even at very low or zero pressure. The choice of desired membrane "cut-off" levels offers selective control of macromolecule transport. The open exterior of the capillaries presents a large surface for cell attachment and allows cells to penetrate toward the barrier at the lumen. The anisotropic fiber membranes may be prepared as described in U.S. Pat. No. 3,615,024. The bundle of hollow fiber capillary units may be prepared as described in U.S. Pat. No. 3,821,087.

While many types of cells have been grown on hollow fiber capillary units, e.g., mouse fibroblasts, human breast and choriocarcinoma, rat pancreas, rat pituitary tumor, rat villus crypt, human hepatocytes, rat hepatoma, monkey kidney, baby hamster ovary, and rat lung, due to the many variables in biologic materials, preparation and operating parameters, specific performance with other types of cells cannot be forecast.

The dialysis membrane may be a parallel flow dialyser such as the Gambro ® Lundia ® Plate.

The following examples illustrate the present invention without, however, limiting the same thereto.

EXAMPLE 1 (comparative)

A unit of capillary bundles (Vitafiber ® Amicon hollow-capillary unit 3S100) a 250 ml reservoir bottle, a finger pump and Silastic tubing (about 2 meters) are autoclaved and assembled under aseptic conditions in the following manner:

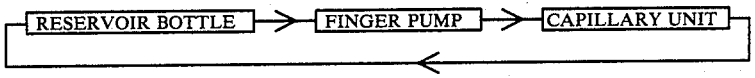

The extracapillary space (2 ml) is charged with a suspension of $3 \times 10^6$ cells of a freshly harvested hepatoma cell line (PLC/PRF/5, MacNab et al., Br. J. Cancer (1976) 34, 509-515). The cells are left undisturbed for 2 hours and then the entire assembled unit is placed in a humidified, 37° C. $CO_2$ incubator. Eagle's Minimum Essential Medium (MEM) containing 10% fetal calf serum, L-glutamine 2 mM, and Neomycin 50 μg/ml is circulated through the capillary unit at a rate of 2 ml/minute. Cell growth is monitored by glucose utilization. Antigen samples are taken from the extracapillary space and assayed by complement fixation. The results together with results from the prior art conventional monolayer tissue culture system are summarized in the following table:

| Age of Cell Culture (days) | Complement Fixation Titers | |
|---|---|---|
| | Capillary System | Conventional Monolayer |
| 6 | <1 | <1 |
| 13 | 4 | <1 |
| 21 | 8 | <1 |

Elimination of the fetal calf serum does not have any significant effect on titers and facilitates further purification of the $HB_sAg$.

EXAMPLE 2

A hollow fiber capillary unit as used in Example 1 is charged with $3-4 \times 10^6$ PLC/PRF/5 cells. The cells are treated as described in Example 1 for two weeks. The temperature of the unit then is reduced to 32° C. and maintained thereafter at this temperature. Daily samples are taken and tested for $HB_sAg$ and for glucose consumption. Complement fixation titers of 1:32 are obtained, whereas at 37° C. usually no titers higher than 1:8 are found. Furthermore, glucose consumption is reduced significantly thus increasing the yield of immunogens per 100 mg of glucose consumed by a factor of 20.

| Age of Cell Culture (days) | Complement Fixation Titer |
|---|---|
| 7 | 1 |
| 14 | 2 |
| 21 | 16 |
| 26 | 32 |

EXAMPLE 3

A hollow fiber capillary unit Vitafiber ® 3S100, is charged with $4 \times 10^6$ cells derived from a higher $HB_sAg$ yielding clone of PLC/PRF/5 cells. Every 30 minutes the hollow fiber unit is turned 180°. After 2 hours MEM containing 10% fetal calf serum, L-glutamine 2 mM and Neomycin 50 μg/ml is circulated through the capillaries at a flow rate of 5 ml/minute. After 2 weeks at 37° C. in a 5% $CO_2$ incubator, the temperature of the unit is lowered to 32° C. and maintained at this temperature for the rest of the experiment. Antigen samples from the extracapillary space are taken and assayed by complement fixation. The results are summarized in the following table:

| Age of cell culture (days) | Complement Fixation Titers |
|---|---|
| 8 | 1 |
| 12 | 2 |
| 16 | 4 |
| 18 | 8 |

EXAMPLE 4

A hollow fiber capillary unit (Vitafiber ® 3S100), is charged with $6-7 \times 10^6$ cells derived from a higher $HB_sAg$ yielding clone of PLC/PRF/5 cells. Every 30 minutes the hollow fiber unit is turned 180°. After 2 hours, MEM containing 10% fetal calf serum, L-glutamine 2 mM and Neomycin 50 μg/ml is circulated through the capillaries at a flow rate of 5 ml/minute. After 2 weeks at 37° C., in a 5% $CO_2$ incubator, a caffeine solution at a final concentration of $10^3$ M is added to the circulating medium. The temperature of the unit is lowered to 32° C. and maintained at this temperature for the rest of the experiment. Antigen samples from the extracapillary space are taken and assayed by complement fixation. The results are summarized in the following table:

| Age of Cell Culture (Days) | Complement Fixation Titers |
|---|---|
| 32 | 64 |
| 39 | 128 |
| 50 | 128 |
| 68 | 256 |

EXAMPLE 5

Hepatoma cells are grown at 37° C. to confluency in plastic, disposable 75 cm² tissue culture flasks. The culture medium is identical to the culture medium used in Example 2. Tissue culture flasks are then transferred to 32° C. and are refed daily. Two flasks serve as a control and are refed with above-mentioned medium. Two other flasks are refed with the same medium which additionally contains $2 \times 10^{-3}$ M caffeine. The supernatants of each group are pooled and samples are tested for antigen by radioimmunoassay. The titers (P/N ratios at 1:16 dilution) are evaluated. Results are summarized in the following table:

| Days Incubation 32° C. | Control Cells | Caffeine treated cells |
|---|---|---|
| 4 | 2 | 6 |
| 9 | 4 | 8 |

What is claimed is:

1. A method for preparing hepatitis B surface antigen which comprises growing cells which shed hepatitis B surface antigen in the presence of a nutrient medium in a first growth stage at a temperature of about 37° C. and a second growth stage at a temperature of from about 30° to 34° C.

2. A method according to claim 1 wherein the first stage takes place at about 37° C. and the second stage takes place at about 32° C.

3. A method according to claim 1 wherein the growing takes place on a permeable membrane.

4. A method according to claim 3 wherein the permeable membrane is a hollow fiber capillary unit or a parallel flow dialyser.

5. A method according to claim 1 wherein the nutrient medium contains caffeine in an amount effective to improve the yield of $HB_sAg$.

6. A method according to claim 5 wherein the caffeine is present in an amount of from about 0.0001 M to about 0.007 M.

7. A method according to claim 1 wherein the cells which shed hepatitis B surface antigen are human hepatoma cells.

8. A method according to claim 6 wherein the caffeine is present in an amount of from 0.001 M to about 0.003 M.

9. A method according to claim 8 wherein the caffeine is present in an amount of about 0.001 M.

* * * * *